US008223429B2

(12) United States Patent
Hoult et al.

(10) Patent No.: US 8,223,429 B2
(45) Date of Patent: Jul. 17, 2012

(54) ACCESSORY FOR ATTENUATED TOTAL INTERNAL REFLECTIVE (ATR) SPECTROSCOPY

(75) Inventors: Robert Alan Hoult, Beaconsfield (GB); Ralph Lance Carter, Towersey Nr Thame (GB); Antonio Canas Wilkinson, New Malden (GB); Paul Styles, Aylesbury (GB)

(73) Assignee: PerkinElmer Singapore Pte Ltd., Singapore (SG)

(*) Notice: Subject to any disclaimer, the term of this patent is extended or adjusted under 35 U.S.C. 154(b) by 826 days.

(21) Appl. No.: 11/912,478

(22) PCT Filed: Apr. 26, 2007

(86) PCT No.: PCT/GB2007/001527
§ 371 (c)(1),
(2), (4) Date: Jul. 25, 2008

(87) PCT Pub. No.: WO2007/122414
PCT Pub. Date: Nov. 1, 2007

(65) Prior Publication Data
US 2009/0002815 A1    Jan. 1, 2009

(30) Foreign Application Priority Data
Apr. 26, 2006    (GB) .................................. 0608258.0

(51) Int. Cl.
*G02B 21/26*    (2006.01)
(52) U.S. Cl. ...................................................... 359/391
(58) Field of Classification Search ........... 359/391–394
See application file for complete search history.

(56) References Cited

U.S. PATENT DOCUMENTS

| 2,960,913 | A |   | 11/1960 | Herrala |
| 4,012,111 | A | * | 3/1977 | Masterson ..................... 359/391 |
| 4,012,112 | A | * | 3/1977 | Masterson ..................... 359/393 |
| 4,681,451 | A |   | 7/1987 | Guerra et al. |
| 4,711,567 | A |   | 12/1987 | Tanimoto |
| 5,019,715 | A |   | 5/1991 | Sting et al. |
| 5,029,791 | A | * | 7/1991 | Ceccon et al. ............. 248/287.1 |
| 5,083,022 | A | * | 1/1992 | Miyamoto et al. ................ 850/1 |
| 5,093,580 | A | * | 3/1992 | Sting ........................ 250/559.16 |
| 5,216,244 | A |   | 6/1993 | Esaki et al. |
| 5,278,413 | A |   | 1/1994 | Yamaguchi et al. |

(Continued)

FOREIGN PATENT DOCUMENTS
EP    0489588 B1    10/1995
(Continued)

OTHER PUBLICATIONS
International Search Report/Written Opinion for PCT/GB07/001527 mailed Jun. 28, 2007.
(Continued)

*Primary Examiner* — Mark Consilvio
(74) *Attorney, Agent, or Firm* — Lando & Anastasi, LLP

(57) ABSTRACT

An accessory for use with a microscope arranged to carry out ATR measurements has a support (40) which can be fixed to the moveable stage (20) of the microscope. A mounting member (100) is carried by the support (40). A sample supporting member (60) is disposed below the location of the ATR crystal (106). The sample supporting member (60) is carried on the support (40) such that it can be moved to restricted extent relative to the support and defines a sub-stage which can be moved relative to the main stage (20) of the microscope.

11 Claims, 7 Drawing Sheets

U.S. PATENT DOCUMENTS

| | | | |
|---|---|---|---|
| 5,347,364 A * | 9/1994 | Kawasaki et al. | 356/445 |
| 5,438,451 A | 8/1995 | Schweizer | |
| 5,517,352 A * | 5/1996 | Hill | 359/368 |
| 5,581,085 A * | 12/1996 | Reffner et al. | 250/339.07 |
| 5,694,930 A | 12/1997 | Pries et al. | |
| 5,729,018 A | 3/1998 | Wells et al. | |
| 5,818,046 A | 10/1998 | Rizvi | |
| 5,943,131 A | 8/1999 | Dausmann et al. | |
| 6,141,100 A | 10/2000 | Burka et al. | |
| 6,466,381 B2 | 10/2002 | Engelhardt | |
| 2001/0009480 A1 | 7/2001 | Engelhardt | |
| 2002/0118448 A1 | 8/2002 | Kirchhuebel et al. | |
| 2003/0031597 A1 | 2/2003 | Sota et al. | |
| 2005/0007547 A1 | 1/2005 | Jones | |
| 2005/0171413 A1 | 8/2005 | Blair | |
| 2006/0077541 A1 | 4/2006 | Zahniser et al. | |
| 2006/0196858 A1 | 9/2006 | Barron et al. | |
| 2007/0170362 A1 * | 7/2007 | Patterson et al. | 250/339.07 |
| 2008/0285122 A1 * | 11/2008 | Hoult et al. | 359/368 |
| 2009/0002815 A1 * | 1/2009 | Hoult et al. | 359/391 |
| 2009/0034065 A1 * | 2/2009 | Hoult et al. | 359/391 |
| 2009/0135477 A1 * | 5/2009 | Noda | 359/391 |
| 2010/0265576 A1 | 10/2010 | Borucki | |

FOREIGN PATENT DOCUMENTS

| | | | |
|---|---|---|---|
| EP | 0730145 A1 | | 9/1996 |
| EP | 0819932 A1 | | 1/1998 |
| JP | 4242145 A | | 8/1992 |
| JP | 4294251 A | | 10/1992 |
| JP | 08233562 A | * | 9/1996 |
| JP | 8313433 A | | 11/1996 |
| JP | 8320289 A | | 12/1996 |
| JP | 9304269 A | | 11/1997 |
| JP | 09304271 A | * | 11/1997 |
| JP | 10325792 A | * | 12/1998 |
| JP | 11166861 A | * | 6/1999 |
| JP | 11166889 | | 6/1999 |
| JP | 2001091452 A | * | 4/2001 |
| JP | 2001133400 A | | 5/2001 |
| JP | 2001235666 A | | 8/2001 |
| JP | 2004354342 A | * | 12/2004 |
| JP | 2005156385 A | * | 6/2005 |

OTHER PUBLICATIONS

International Search Report/Written Opinion for PCT/GB07/001528 mailed Jul. 4, 2007.

International Search Report for PCT/GB07/001530 mailed Jul. 31, 2007.

Partial International Search Report for PCT/GB07/001531 mailed Aug. 16, 2007.

* cited by examiner

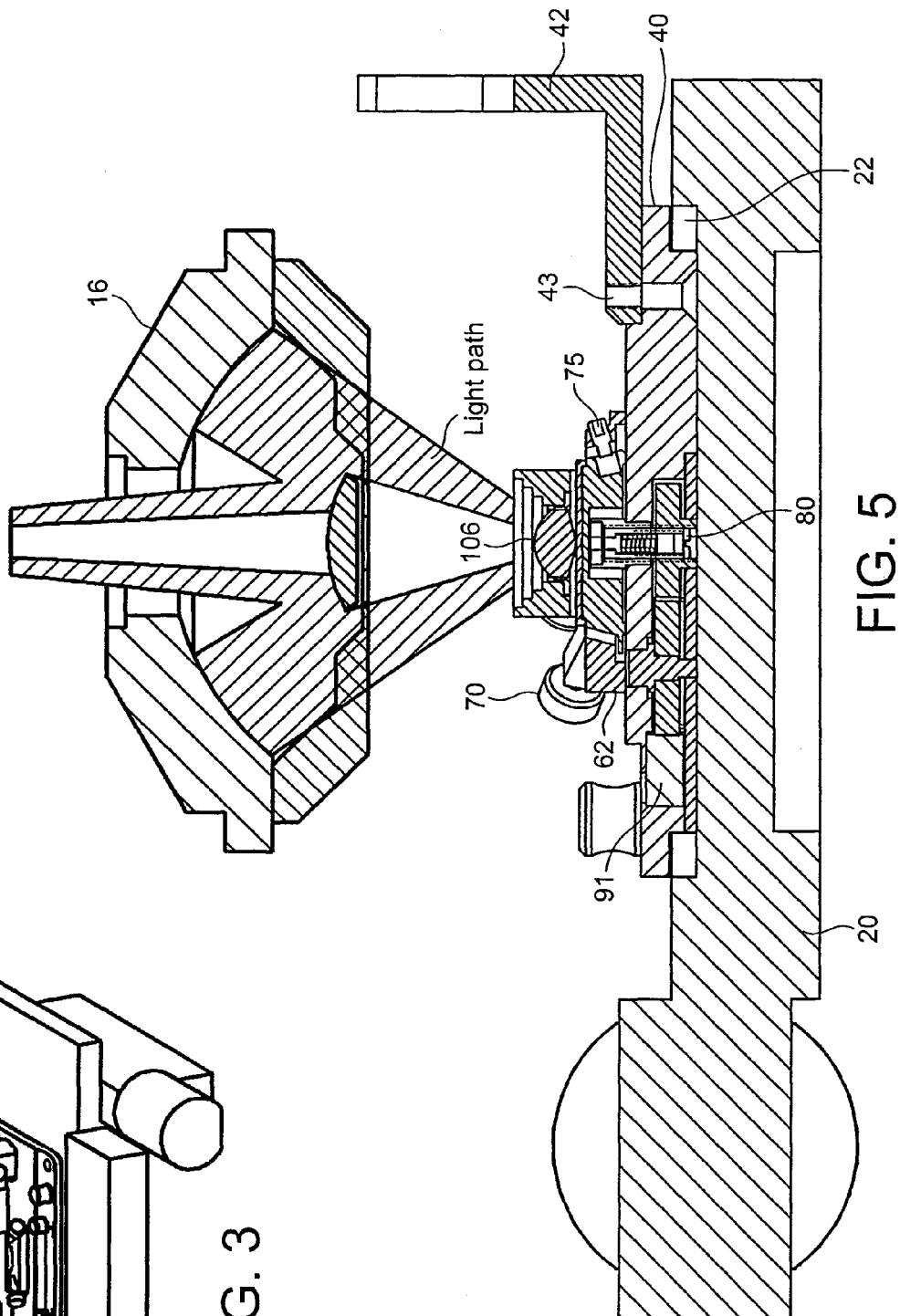
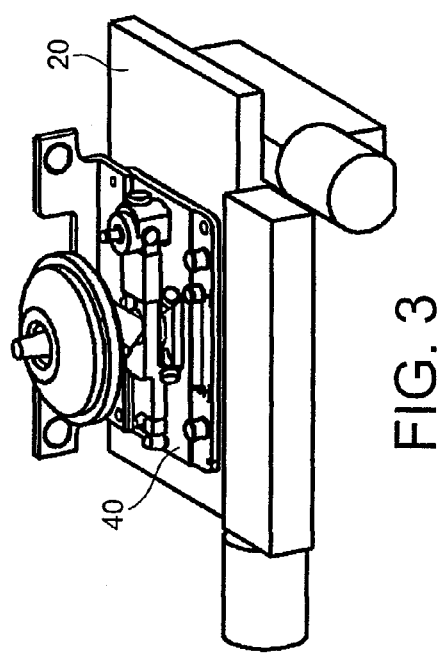
FIG. 5
FIG. 3

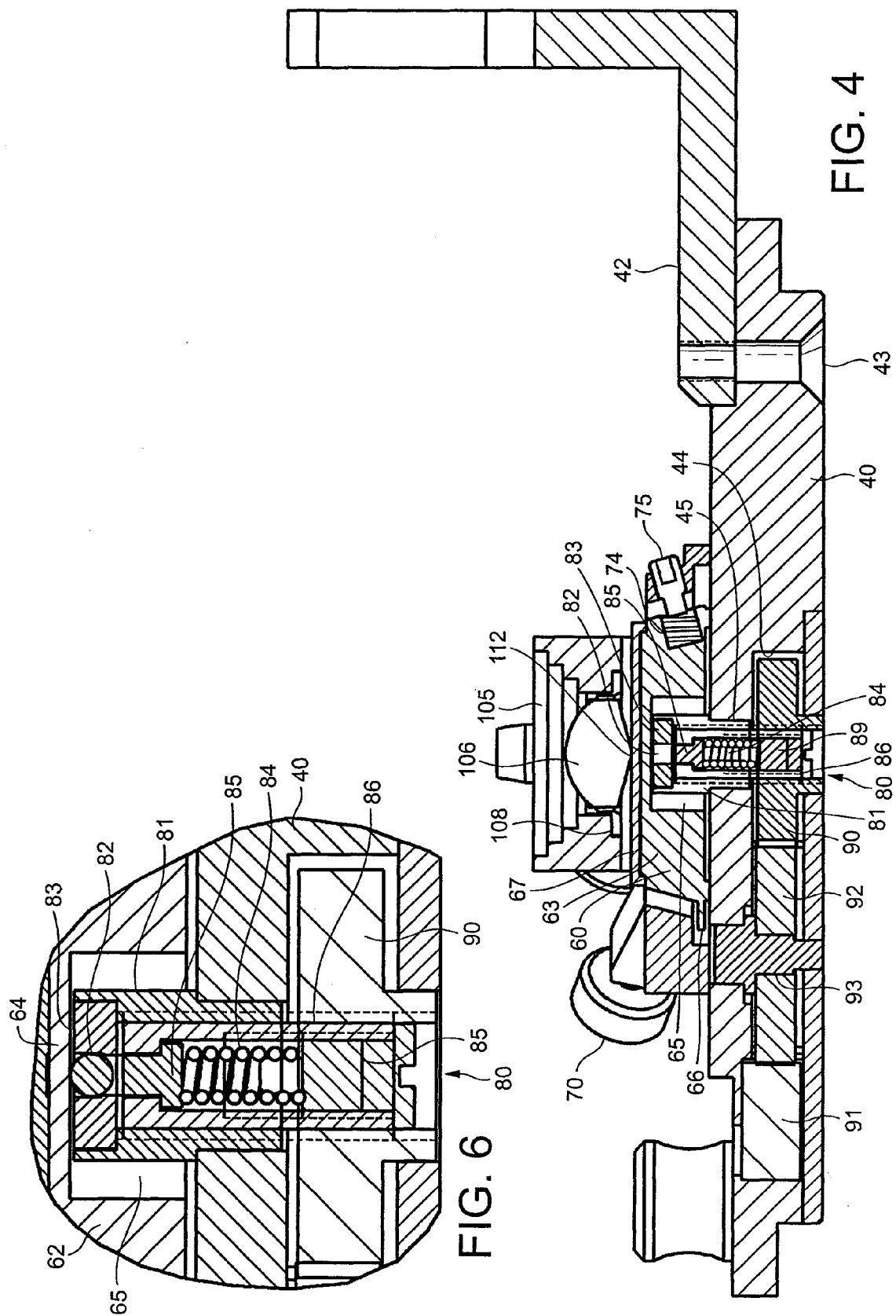

ACCESSORY FOR ATTENUATED TOTAL INTERNAL REFLECTIVE (ATR) SPECTROSCOPY

This application is a national stage application that claims priority to PCT/GB07/01527, filed on Apr. 26, 2007. PCT/GB07/01527 claims priority to UK Application No. 0608258.0 filed on Apr. 26, 2006.

This invention relates to spectroscopy which makes use of attenuated total internal reflection (ATR).

ATR is a technique used in spectroscopy, such as FT-IR spectroscopy, in order to obtain spectral measurements from samples which are difficult to analyse by other means such as transmission or reflection. Typically apparatus for carrying out ATR measurements will comprise a spectrometer to provide wavelength discrimination, an illumination system for directing light onto a sample, an ATR optic which provides a sample plane and a collecting/detecting system which receives light which has interacted with the sample. The ATR optic is arranged in such a way as to reflect all incident light from a designated sample plane by means of the phenomenon of total internal reflection. Spectral information concerning the sample is derived from the interaction of the sample with an evanescent electric field that exists immediately outside the reflecting surface. The absorption of energy from this field attenuates the reflection and impresses spectral information on the light beam.

An imaging ATR system can be constructed based upon these principles by arranging to illuminate an area of a sample and by arranging the collecting system to have imaging properties. Light returning from spatially distinct regions of the sample is collected on a detector or a detector array such as a one dimensional or two dimensional array of detectors and spectral information is thus collected which can be compiled into a spectral image of sample.

An imaging ATR system can be constructed in the form of a reflectance microscope such as the Perkin Elmer Spotlight microscope. In such an arrangement light is directed onto and collected from a reflective sample by means of an imaging optic. An ATR optic for such a system can conveniently comprise a hemispherical plano-convex lens made of a high refractive index material such as germanium. The optic is arranged so that the convex spherical surface is directed towards the microscope optic with its centre of curvature arranged to be coincident with the focal plane of the imaging system. The sample is presented to the flat surface of the ATR.

The microscope includes a moveable stage which has associated motors for moving the stage in x, y and z directions under processor control. Imaging is carried out using a small linear array detector and physically moving the stage and therefore the crystal/sample combination laterally relative to the optical axis of the microscope. As the stage is moved images can be detected by the detector from different parts of the sample and in this way a spatial image can be accumulated.

There are a number of requirements and problems which arise in this type of arrangement. The region of interest of the sample has to be identified usually visually and placed approximately at the centre of the field of view of the microscope. This usually means removing the ATR crystal since it is usually made of material such as germanium which is opaque to visible light.

The ATR crystal has to be placed with its sample contacting face in intimate contact with sample. This can lead to problems in achieving an infrared image which is in focus. The sample may move when the crystal is brought into contact with it. Also the crystal may cause defocus by virtue of its shape. For example if the thickness of the crystal is not precisely the same as its radius of curvature. The effect is magnified because the material of the crystal has a high refractive index of around 4. Therefore small manufacturing errors can be significant.

The present invention is concerned with improvements in arrangements for ATR spectroscopic systems which attempt to overcome these and other problems.

According to a first aspect of the present invention there is provided an accessory for a microscope arranged to carry out ATR measurements, said accessory comprising a support which can be mounted on the movable stage of the microscope, a mounting member for mounting an ATR crystal carried on said support, said mounting member being so mounted and arranged on the support that it can be moved between a position in which a crystal mounted on the mounting member is aligned with the optical axis of the microscope and a position in which the crystal is displaced from the optical axis.

The mounting member may comprise an elongate an pivotally supported at one end on a first guide pin, said arm being pivotal about said pin to allow said movement of the mounting member.

The other end of the arm may have an opening which engages a second pin carried by the support member when the mounting member is located in the position in which the crystal lies oil said optical axis.

The arm may be raised along the axis of the first guide pin so that said other end moves clear of the second guide pin to allow said pivotal movement.

A braking mechanism may be associated with said one end of the arm and said first guide pin, said braking mechanism being operative to allow a controlled descent of the arm along the first guide pin when said arm is returned to its position in which the crystal is aligned with said optical axis.

The braking mechanism may comprise a ring which is carried by said arm and locates around said first guide pin, said ring having an inner diameter which is slightly greater than that of said first guide pin, biasing means operative to bias said ring so that a circumferential portion thereof frictionally engages a surface part of the guide pin, and manually operable means operable to act against said bias means to reduce or release said frictional engagement and thereby allow axial movement of the ring relative to the guide pin.

The mounting member may be carried in such a way that it can be removed from its mounting and inverted by rotation about its longitudinal axis to allow inspection of the sample engaging surface of the crystal, for example to check that the crystal is not damaged or contaminated.

This aspect of the invention by use of the movable mounting member allows the crystal to be mounted on the microscope stage such that is can be removed and subsequently returned accurately and reproductively to its original position.

According to a second aspect of the present invention there is provided an accessory for a microscope arranged to carry out ATR measurements, said accessory including a support which can be mounted on the movable stage of the microscope, a mounting member in which is mounted an ATR crystal, said crystal having a sample contacting area, and a registration indicium located such that it is fixed relative to the sample contacting area. The crystal may have a generally hemispherical surface opposite to said contacting area and said registration indicium may be located at the apex region of the hemispherical surface. The indicium may comprise a flat on the hemispherical surface or a mark on the hemispherical surface.

According to a third aspect of the present invention there is provided a method of operating a microscope provided with an accessory according to said second aspect said microscope including processing means for controlling movement of the movable stage and said processing means having recorded therein a predetermined parameter relating to the height of the ATR crystal, said method comprising initially moving the stage of the microscope to bring the registration indicium into focus and moving the stage by a predetermined vertical distance defined by said parameter in order to bring into focus a sample contacting said sample contacting area.

According to a fourth aspect of the present invention there is provided a method of calibrating an ATR crystal for use with a microscope according to said second aspect or a method according to said third aspect said method comprising a selecting a test sample which exhibits strong absorption within the spectral range of the microscope and which has a geometry which will produce sharp spatial edges when contacted by an ATR crystal, said method comprising bringing the sample contacting area of the crystal into contact with the test sample, acquiring an infra-red image of the test sample at an initial vertical position of the crystal, processing the image to extract slope information for said edges, repeating the process for different vertical positions of the crystal, identifying the optimum vertical position as that which exhibits the maximum slope, and deriving a calibration parameter for said crystal according to said identified optimum position.

The processing may include, for each vertical position, spectrally filtering the acquired image to extract a spatial map of the absorbance at a wavelength where the test sample absorbs strongly.

The method may include extracting a cross-section which traverses the spatially sharp features of the absorbance map at said wavelength.

The method may include differentiating the cross-section to extract said slope data, and measuring the maximum slope for a recognisable feature in the image.

The text sample may be a plastic material such as a micro-embossed polymer, e.g. Vikuiti brightness enhancing film.

The second, third and fourth aspects of the invention provide a facility which allows determination of the optimum position of the crystal with respect to the microscope and which can cope with manufacturing tolerances of the crystal. It can position the crystal at the optimum vertical position for achieving a focussed infra-red image in a reproducible manner irrespective of sample thickness.

According to a fifth aspect of the present invention there is provided all accessory for a microscope arranged to carry out ATR measurements, said accessory including a support which can be mounted on the movable stage of the microscope, a mounting member carried on said support for mounting an ATR crystal, a sample supporting member disposed below the location of the ATR crystal, said sample supporting member having a surface upon which a sample can be received, and pressure applying means disposed below said sample supporting member for applying a pressure to said sample supporting member in the direction of said crystal.

The pressure applying means may include a spherical member through which pressure is applied to said sample supporting member. This permits limited tilt of the supporting member in order to accommodate irregular samples.

The pressure applying means may include spring bias means.

The spring bias means may include a plunger which is urged towards the crystal by a spring.

The spherical member may be a ball bearing and said plunger contacts said ball bearing.

The accessory may include a rack and pinion arrangement coupled to said plunger, said rack being movable manually to effect rotation of the pinion to cause axial movement of the plunger to thereby apply or release pressure applied to the sample supporting member.

The pressure which can be applied to the sample supporting member may be adjustable.

The area of the sample supporting member through which the pressure applying acts is relatively thin to ensure that the point at which the pressure is applied is as close as possible to the crystal.

This aspect of the invention provides a simple and effective means for ensuring that the sample is held in good contact with sample contacting surface of the crystal.

According to a sixth aspect of the present invention there is provided an accessory for a microscope arranged to carry out ATR measurements, said accessory comprising a support which can be fixed to the movable stage of the microscope, a mounting member carried by said support for mounting an ATR crystal, a sample supporting member disposed below the location of the ATR crystal, said sample supporting member defining a sample receiving surface, said sample supporting member being carried on said support so that it is movable relative to the ATR crystal and defines a sub-stage which can be moved relative to the main stage of the microscope.

The sample supporting member may comprise a flat upper surface and side surfaces and the accessory includes location adjusting means for adjusting the position of the sample supporting member on the support.

The location adjusting means may comprise a pair of screws acting to urge the member against a biasing spring.

The screws may be located so as to act along orthogonal directions and said spring is arranged to act along a bisector of said directions.

The surface against which each screw acts may be at a small angle to an axis through the crystal whereby each screw acts to urge the sample supporting member towards the support.

The aspect of the invention provides a sub-stage which allows the position of the sample to be adjusted without affecting any previous setting of the main stage of the microscope.

It will be appreciated that the features of the various aspects of the invention defined above can be used in any combination thereof.

The invention will be described now by way of example only with particular reference to the accompanying drawings. In the drawings:

FIG. 3 is a perspective view showing the accessory located in the movable stage of a microscope;

FIG. 4 is a section on the line Z-Z of FIG. 2,

FIG. 5 is a section similar to FIG. 3 showing the location of the accessory in a microscope in relation to the objective cassegrain lens, and FIG. 6 is a section on a larger scale of part of FIG. 4;

Figure 1:
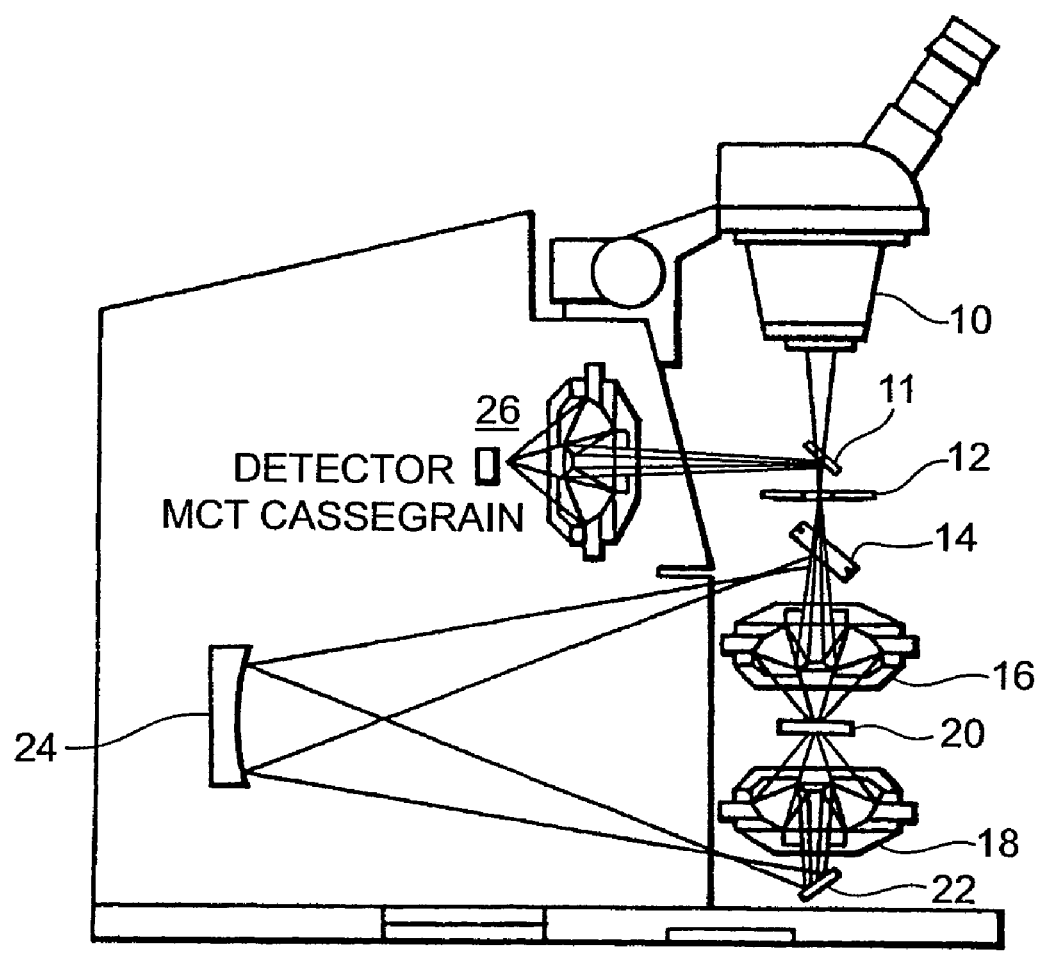
FIG. 1 is a schematic side view illustrating the principal elements of a known FT-IR microscope.

Referring to FIG. 1 this shows the principal elements of an FT-IR microscope and these include an optical microscope 10 which is disposed above a view/IR mirror 11 which in turn is disposed above a remote aperture 12. Located below the remote aperture 12 is a transmittance/reflectance mirror 14 which is positioned above an objective cassegrain assembly 16 and a condenser cassegrain assembly 18. Between the two cassegrains is disposed a movable stage 20 which defines the position of the sample for analysis. Located below the condenser cassegrain 18 there is a flat mirror 22 which can direct radiation from a coupling optic 24 which is in turn configured to receive radiation from a radiation source. A microscope of this type can be used for both reflectance and transmission measurements. The condenser cassegrain 18 and the flat mirror 22 are used primarily for transmittance measurements. For reflectance measurements the coupling optic 24 is tilted to direct the radiation to the transmittance/reflectance mirror 14 which then directs a substantial part of the radiation down through the objective cassegrain 16 on to the sample. The radiation is reflected from the sample back through the objective cassegrain 16. It is the reflectance mode with which embodiments of the present invention are concerned. The apparatus also includes a detector and a cassegrain arrangement 26 which is used to carry out the spectroscopic analysis in conjunction with an IR spectrometer not shown. The operation of an arrangement of this type will be known to those skilled in the art and more details of the operation of such an arrangement as used in conjunction with an ATR crystal can be found for example in EP-A-0730145 and EP-A-0819932.

The present description is concerned with an accessory which can be located on the movable stage 20 of a microscope to enable ATR imaging measurements to be carried out. Referring to FIGS. 2 to 9 of the drawings an embodiment of the accessory comprises a support in the form of a baseplate 40 which is connected to a bracket 42 by means of screws 43. The baseplate 40 locates in a recess 22 formed in the movable stage 20 of the microscope. The stage 20 is movable in x, y and z directions under processor control by means of appropriate motors as will be known to those skilled in the art. The baseplate 40 is held in position in the recess 22 by means of screws which are not shown in the drawings. The bracket 42 provides a means of holding the accessory when locating it on or removing it from the stage 20.

The lower surface of the baseplate 40 is recessed at 44 and a bore 45 extends through the baseplate and communicates with the recess 44.

Figure 2:
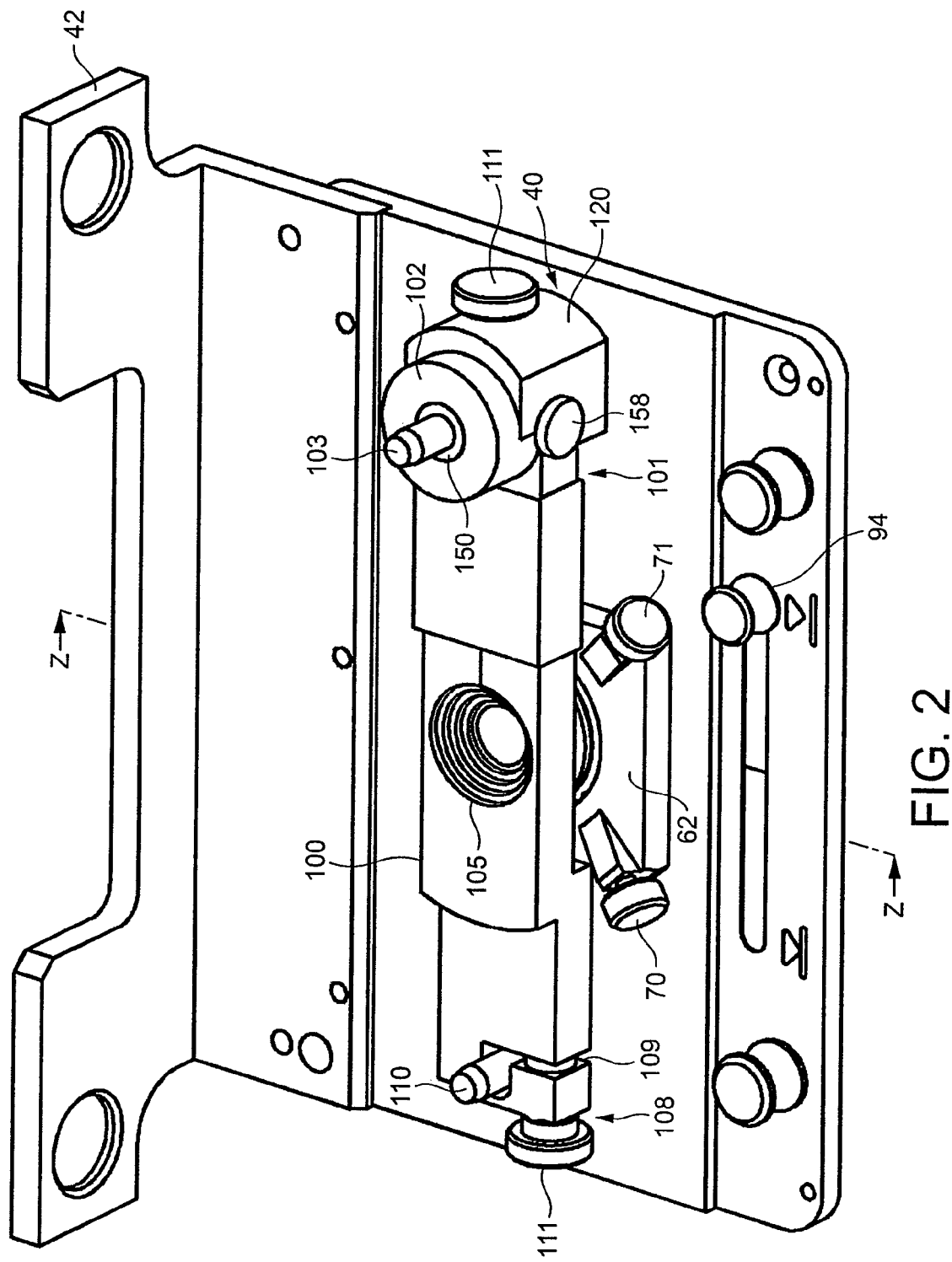
FIG. 2 is a schematic perspective view of an accessory for an ATR microscope, said accessory being constructed in accordance with one embodiment of the present invention.

The upper surface of the baseplate 40 supports an anvil 60 which comprises a sample supporting member. The anvil 60 is generally circular in plan and is located within the circular opening in a collar 62. The outer edge of the collar, as can be seen in FIG. 2, is generally square and the inner circular opening in the collar is slightly larger than the outer circular surface of the anvil so that the anvil can move to a restricted extent within the confines of the collar.

The anvil has a relatively thick annular side wall 63 and a relatively thin top wall 64. A recess 65 is defined between the top wall 64 and the side wall 63. The top surface of the anvil carries a removable plate 67, the top surface of the plate 65 constituting a sample supporting surface. A projection 66 extends radially outwardly from the wall 62 to locate beneath an overhanging part of the collar. This arrangement allows a small vertical movement of the anvil.

The anvil is held in place within the collar by means of two manually operable adjusting screws 70, 71 located towards the front of the collar and a spring 74 (FIG. 4) disposed at the rear of the collar. The spring is held in place by a screw 75. The screws 70, 71 are arranged so that their axes extend orthogonally towards the axis of the anvil and the spring 74 is designed to act along a bisector of the angle between the axes of the screws. Thus, by manually operating the screws 70, 71 it is possible to cause movement of the anvil within the confines of the collar 62. Each screw is arranged to act against a surface on the anvil, which surface is inclined at a small angle to an axis through the anvil. The spring 74 is also arranged to act at a slight angle and this arrangement ensures that there is a small vertical force imparted to the anvil which acts to press the anvil towards the baseplate 40.

The anvil arrangement described above constitutes a sub-stage which can be moved relative to the electronically movable stage 20 of the microscope itself.

A pressure exerting mechanism 80 for exerting pressure on the underside of the top wall 64 is disposed below the anvil 60. The pressure exerting mechanism includes a tubular insert 81 which is threaded internally and which locates within the bore 45 of the baseplate. At its upper end, the threaded insert 81 accommodates a ball bearing 82 which is disposed in a ball guide 83. The ball bearing is biased upwardly into contact with the underside of the top surface 64 by a spring 84 which pushes on the ball by way of a top-hat plunger 85. This plunger 85 is disposed in a plunger guide tube 86 threaded within the tubular insert 81 and extending downwardly into the recess 44. The spring is retained in the guide 86 by means of a screw 89 which can be used to adjust the pre-load of the spring.

A pinion gear 90 is fixed around the lower end of the guide tube 86 and connected to the screw. The pinion gear 90 is coupled to a rack 91 by way of an idler gear 92 which can rotate about a spindle 93. The rack can be moved longitudinally by means of a manually operable knob 94 shown in FIG. 2. When the rack is moved longitudinally this causes rotation of the pinion gear 90 and this in turn causes a corresponding rotation of the spring plunger retaining guide tube within the tubular insert 81. Depending upon the direction of movement of the rack, rotation of the retaining guide tube 86 raises or lowers the tube 86 thereby either applying a lifting force through the ball 82 to the anvil or allowing the anvil to fall.

A mounting for an ATR crystal is carried above the anvil 60. This mounting comprises an elongate arm 100 supported at its opposite ends. The arm has a first end 101 with an annular formation 102 within which is located a pair of bushings and which locates over a guide pin 103 carried on the baseplate 40. The arm also has a central portion with an aperture 105 which has stepped sides. The aperture comprises the location for an ATR crystal 106 which is shown in FIG. 4.

The arm has a second end 108 which is located at a level lower than that of the first end. The second end 108 has an L-shaped slot 109 which can receive a second guide pin 110 carried on the baseplate 40. Locking screws 111 are provided to lock the arm 100 in position on the guide pins.

Figure 9:
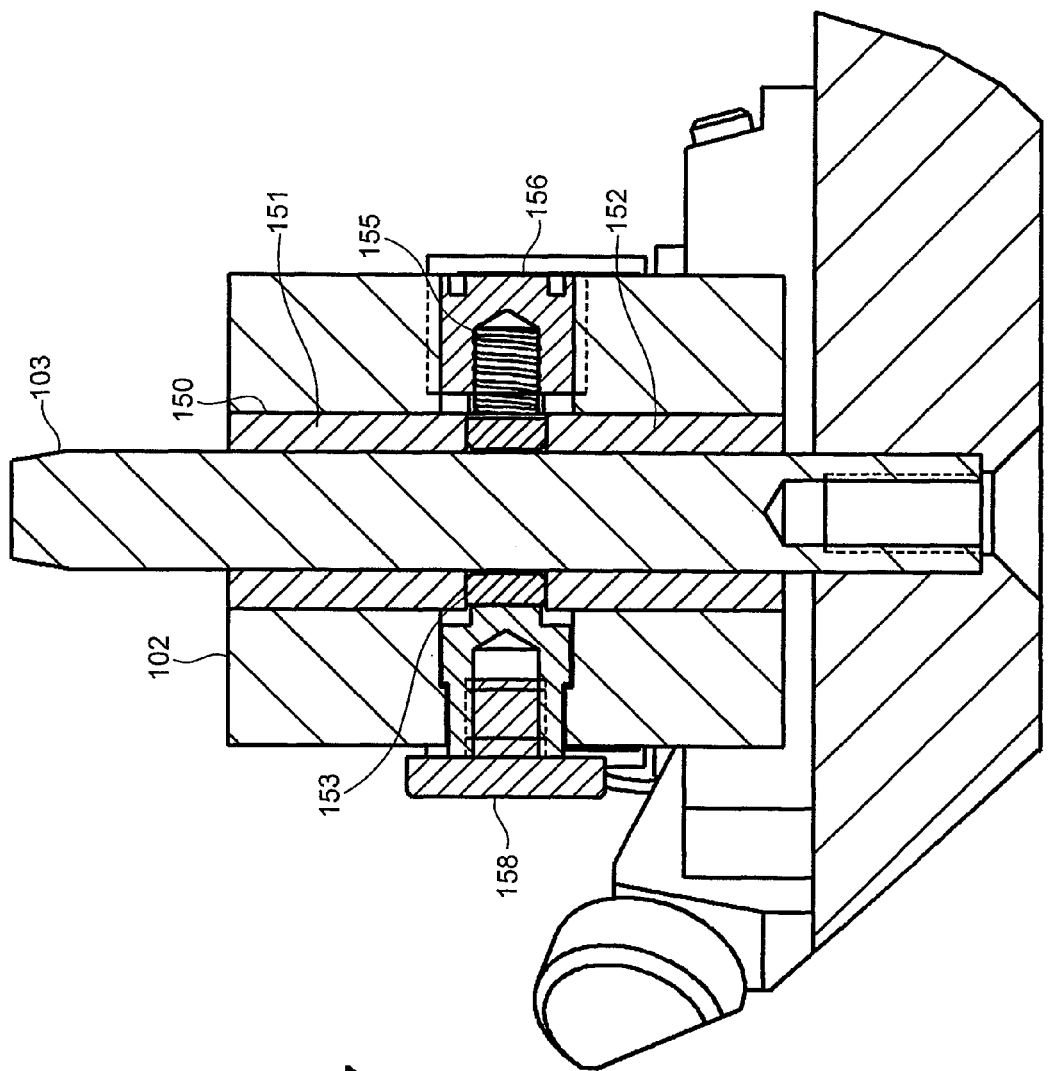
FIG. 9 is a section on the line W-W of FIG. 7.
Figure 7:
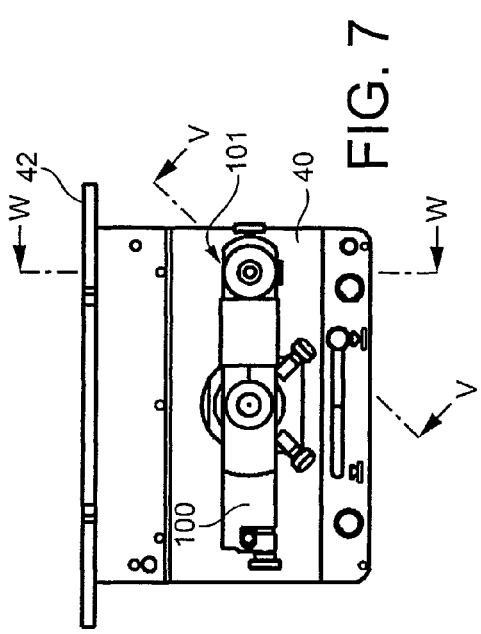
FIG. 7 is a plan view of the accessory.

The first end 101 of the arm 100 is provided with a braking mechanism which operates in conjunction with the guide pin 103. Referring to FIG. 9 the annular formation 102 has a split internal bushing 150 with upper and lower parts 151 and 152. A rigid braking ring 153 is disposed between the bushing parts 151 and 152. The internal diameter of the braking ring is slightly greater than the external diameter of the guide ring 103. The ring 153 is usually biased into contact with the pin 103 by a spring 155 which is held in position in the annular formation 102 by a spring retainer and brake release stop 156. Diametrically opposite to the spring there is provided a brake release button 158 which is held captive in the annular formation 102. The radially inner end of the button 158 locates against the braking ring 153. When the button 158 is pressed the ring 153 is moved radially to a position where no part of it is in contact with the pin 103 thus releasing the braking effect. The mechanism 156 limits the extent to which the ring 153 can be moved.

Figure 8:
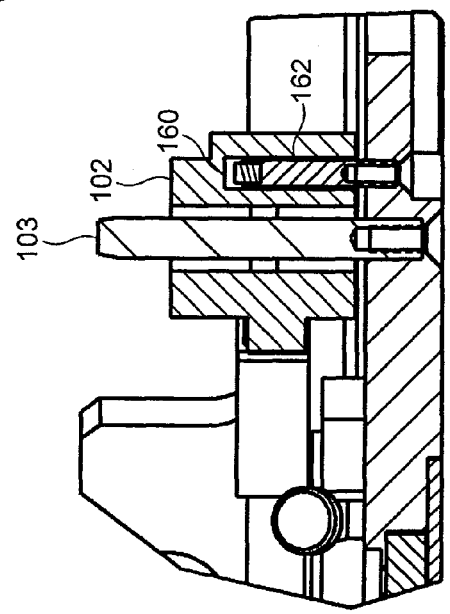
FIG. 8 is a section on the line V-V of FIG. 7.

Referring to FIG. 8 the annular formation 102 also includes an axially extending bore 160 which is spaced radially from the pin 103. The bore 160, when the arm 100 is in the position shown in FIG. 2, receives an upstanding support pin 162 carried on the base 40. If the arm 100 is raised along the axis of the pin 103 so that the bore 160 moves clear of the pin 162, the arm 100 can then be rotated about the guide pin 103 away from the position shown in FIG. 2. The pin 162 can then contact the underside of the arm 100 to hold it in its raised position. The arm 100 can be rotated back to the position shown in FIG. 2 and allowed to lower to its original position when the pin 162 and bore 160 are aligned. The arrangement of pin 162 and bore 160 in conjunction with the location of the guide pin 110 in the slot 109 ensures correct and reproducible location of the arm 100 and therefore correct and reproducible location of the crystal 106 on the optical axis of the microscope.

The crystal 106 is generally hemispherical and is made from germanium. The lower surface is generally in the form of a shallow cone and has a flat central area 112 which constitutes a sample contacting area. The crystal 106 is bonded within a mounting ring 108 which is held within the opening 105 in the arm 100. The arm can include a sliding dust cover (not shown) to cover the crystal when not in use.

In use the crystal is positioned with respect to the microscope so that the centre of sample contacting area 112 is substantially at the focus of the microscope. Where an ATR crystal is to be used for ATR imaging optimisation of the crystal design is important. When carrying out ATR imaging as distinct from simple transmission or reflectance imaging a wider field of illumination is required. Furthermore, in the case of an imaging system which involves scanning, the illumination may well be non-uniform across the field of view so that some compensation has to be made for this if effective clear images are to be obtained. Whilst this can be achieved in software, optical modelling work carried out by the inventors has shown that the radius of curvature of the crystal affects the uniformity of the illumination. It has been found that an optimum radius exists for a given arrangement of illumination optics and detector such that variations across a designated image area can be minimised whilst throughput is maintained. This technique has shown that a crystal radius of 6.75 mm is an optimum for the arrangement shown in the drawings. This figure can be arrived at by using a Ray tracing technique in conjunction with appropriate assumptions which take into account polarisation effects. It is found by operating this procedure that for a small radius of curvature on the ATR optic the energy received from the centre of the sample area is high but the energy received from the other parts is relatively low. The image of the sample is thus highly spatially non-uniform in brightness even if the sample itself is spatially uniform. As the radius of curvature of the ATR optic is allowed to increase the uniformity of signal across the sample area improves to a point where the signals from the centre and the edges are approximately equal. The uniformity of illumination defined in this way can be used as a metric by which to select an optimum radius of curvature. If the radius of curvature is allowed to increase further the total energy received from all points of the sample area is typically seen to increase initially passing through a peak value at a certain radius of curvature and then falling away again to a very large radius. The radius at which the peak total energy occurs can be selected as the design optimum referred to above.

The mounting of the arm 100 on the guide pins 103, 110 in the manner shown in the drawings enables the arm 100 to be removed from the guide pins by raising it upwardly. The arm can then be inverted about its longitudinal axis, and replaced on the guide pins so that the sample contacting surface of the crystal is uppermost. This 110 enables the sample contacting surface of the crystal to be inspected using the visual inspection facility of the microscope to thereby allow its condition to be assessed. The arrangement of guide pins 103, 110 also allows the arm to be raised and then pivoted about pin 103 to allow the crystal to be moved out of the optical path of the microscope. This can occur because the top of guide pin 110 is lower than the guide pin 103. In this position the arm 100 is held in its raised position by the pin 162. The slot 109 allows accurate relocation of the arm 100 by locating the pin 110 in the slot 109. The locking screws allow the arm to be locked at a selected height, for example with the crystal in contact with a sample.

Additionally, the crystal 106 is provided with a registration mark at the apex of the hemispherical surface. This mark can take the form of a flat formed on the hemispherical surface or some other form of marking on the surface itself. This registration mark is used to correctly locate the crystal both horizontally and vertically as will be described.

The registration mark does not have to be at the apex of the hemispherical surface although this is the most convenient and preferred position. The mark can be at any location on the accessory provided that that location is fixed mechanically relative to the sample contracting area 12 and is visible through the viewing system of the microscope.

As can be seen from the drawings the arm 100 when it is located on the baseplate 40 needs to be lowered towards the sample receiving surface. It is important that this movement be controlled in order to avoid damage particularly to the crystal and to this end the accessory is provided with the brake mechanism 153, 155, 156, 158 located within the structure 120 which includes the guide pin 103. The brake mechanism normally prevents the arm from dropping under gravity and is provided to avoid inadvertent damage to the crystal 106. The button 158 is operated manually to release the brake and allow the arm 100 to be lowered. The use of a releasable braking mechanism enables a user to lower the arm without any friction between the arm and guide pin and therefor gives the user greater control of the lowering operation.

The registration mark provided preferably at the apex of the crystal 106 is used to align the crystal with the optical axis of the microscope thereby providing a defined starting position for any imaging scan. The software of the instrument is provided with lateral offset parameters which permit an ATR image to be aligned precisely with the visible light image or with a conventional transmission/reflectance image. Also the software is provided with a precalibrated crystal height parameter which defines the distance by which the crystal 106 and sample should be raised from an initial position in order to bring the sample surface into sharp focus via the infrared part of the microscope system. This is significant because the crystal 106 is opaque to visible light and manual sample focusing is not possible when the crystal is in place.

Figure 10:
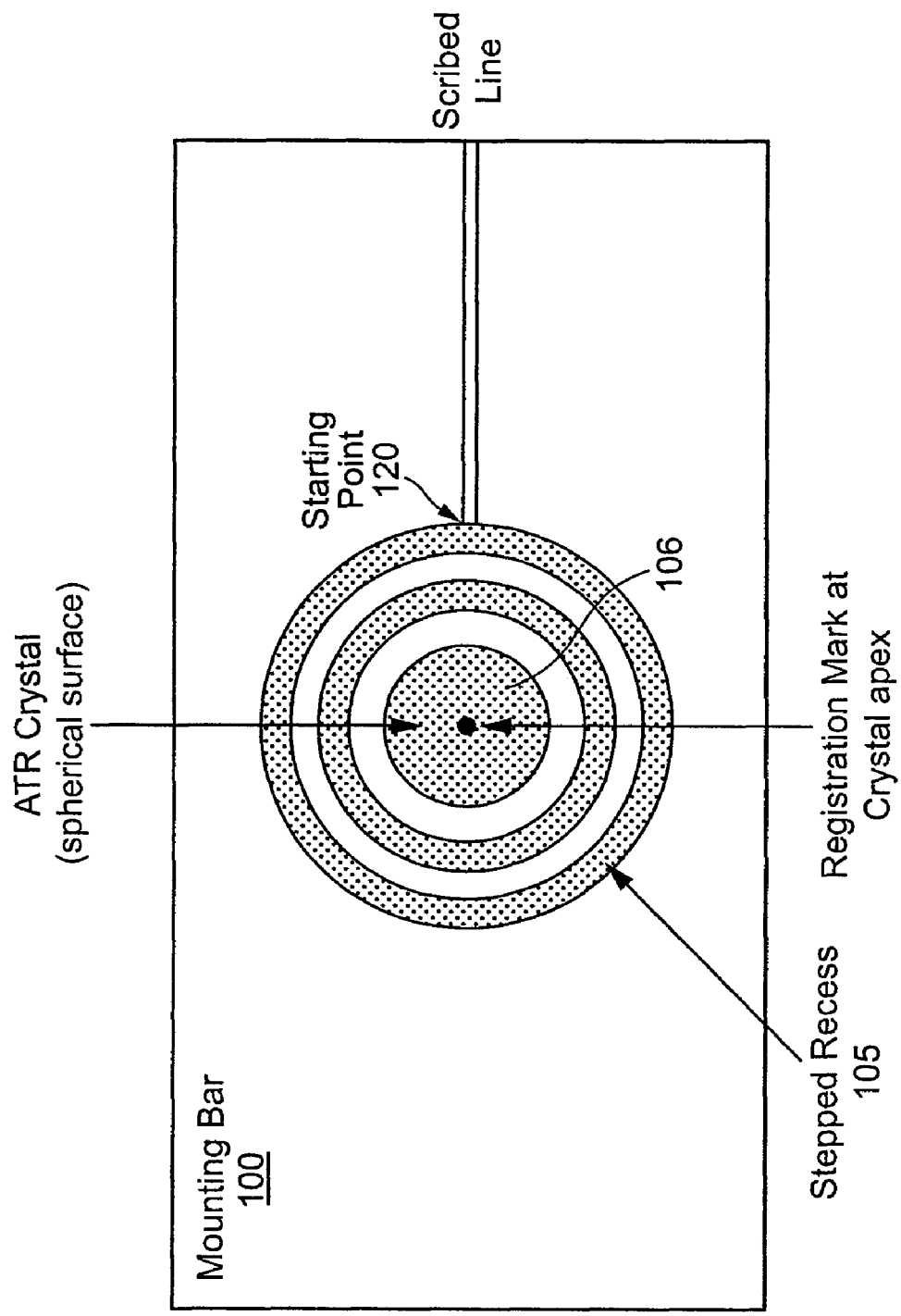
FIGS. 10 and 11 illustrate the operation of an imaging microscope which incorporates the accessory.

In order to register the crystal position, the crystal 106 and its mounting arm 100 are located above the sub-stage or anvil with no sample in position. The user of the instrument is prompted to focus using the visible camera on a point on the arm 100 known as the starting point. This is illustrated at 120 in FIG. 10 of the drawings. The system then operates to move by a predetermined distance in an x, y z co-ordinate system to the centre of the top of the crystal which is fiducial or registration mark. The user then confirms that the centering and focus are correct making any small adjustments that may be required. The system then sets the stage co-ordinate system origin (0,0,0) as the confirmed position.

The calibration of the crystal height and focus setting can be carried out as follows. In this respect it needs to be appreciated that small variations in the crystal shape (radius of curvature and thickness) can give rise to significant shifts in the required focus setting. As the refractive index of germanium is high, focus cannot be established visually because the crystal is opaque to visible light and it requires a sample with a well defined spatial structure as well as a strong spectral absorption band that can be detected by ATR. A novel method has been developed by the inventors whereby the optimum ATR focus setting can be determined. This method makes use of a test sample which preferably comprises a small section of 3m Vikuiti BEF 11 film. This is a plastic sheet the surface of which is micro embossed with a set of parallel triangular prisms each of which has a 90° apex angle and a period of 50 or 24 microns. The material is commonly employed to improve the brightness of LCD display panels. The ATR crystal is brought into contact with the prism structures so that the apices are flattened by the contact pressure thereby resulting in a set of parallel rectangular contact zones with the same pitch as the basic material. Each zone has sharp edges. In order to determine the optimum focus small fine resolution images are acquired around the centre of the field and narrow waveband images are extracted which are centred on the material's spectral absorption. The technique involves extracting absorption image cross sections orthogonal to the edges. The degree of focus is estimated by inspecting the slopes of the cross sections across the contact edges. Measurements are taken at various vertical positions of the crystal and the slopes increase as optimum focus is approached and drop away again when departing from the optimum focus. The best position can be found by interpolating between a set of scans taken at different focus settings. It should be noted that the deformation of the sample film depends upon the contact pressure and this can be used as a means of confirming that adequate pressure is being applied to the sample.

Thus in more general terms crystal calibration is achieved by using a test sample with particular properties and examining infra-red images of this sample for spatial sharpness. The vertical displacement of the crystal is varied in steps and image sharpness is recorded at each step in order to determine an optimum displacement. This involves
  a) An infra-red image is acquired at an initial vertical displacement which is estimated by finding the position at which maximum infra-red energy is transmitted through the crystal. This may not be the same as the best focus position.
  b) The image is spectrally filtered to extract a spatial map of the absorbance at a wavelength where the sample absorbs strongly. This is a function of the material properties.
  c) A cross-section of the absorbance map at this wavelength is extracted which traverses spatially sharp features in the image—in the present case an edge between a polymer and air.
  d) The cross-section is differentiated mathematically to extract slope information, and the maximum slope is measured for a recognisable feature in the image.
  e) The crystal displacement is adjusted iteratively so as to maximise the slope of the cross-section at the given feature. The vertical crystal position where maximum slope is obtained is the position at which the image of the sample is in best focus. This value (measured with respect to the index mark) is recorded as the crystal height parameter which is supplied to a user.
  f) Any new/replacement crystal will have a new calibration value which a user must input to the control software of the instruments.

In principle the test sample can be any material with infra-red absorption which can provide spatially sharp features which are ideally small compared to the anticipated spatial resolution of the microscope system. This means typically features which are sharp on a scale of about 3 microns.

The test sample should be "ATR-compatible"—in other words it should provide a clear spectral absorption within the spectral range of the ATR accessory and the sharp features must survive being pressed into intimate contact with the sample surface without becoming smeared out or smoothed.

The sharp features might include engineered fine structures such as lines, gratings or grids, or alternatively sharp edges between two different materials (one of which might be air in the form of a void). If the features are constructed by forming indentations in a uniform material, then the indentations should have a depth of more than a few microns when in contact with the crystal, and the transitions from contact to non-contact should be sharp.

As explained above the presently preferred material is a particular micro-embossed polymer sample (Vikuiti light control film manufactured by 3M) because it provides a convenient, cheap and reproducible test sample. The material comprises a regular array of roof prisms whose ridges are conveniently flattened by contact with the crystal to leave straight "bars" of contact. The geometry of the edges of these contact regions is such that the material drops away from the crystal rapidly, especially over the first few microns of depth, and this yields a very high quality edge between absorbing polymer and non-absorbing air which is easily imaged using ATR to give high-contrast and sharp results.

The inventors have also developed a technique for definition of spatial resolution. The technique described above for determining the optimum focus of the crystal can be adapted to provide a measurement of the effective resolution of the ATR system in a manner which is difficult to achieve on systems which employ staring two dimensional array detectors. Having determined an optimum focus setting as described above, a small strip image is acquired across one or more of the edges in the test target but using a very fine step in the direction across the edges. This results in an image which is over-sampled in this direction. A cross section is extracted in the absorption band of the sample and differentiated by means of a digital filter. The profile thus obtained approximates to a cross section through the point spread function of the optical system and can be used to estimate the resolving power of the system either directly or via appropriate curve fitting.

In order to carry out measurement of a spectrum on a sample the first step is to register the crystal position and define the stage co-ordinate system origin (0,0,0) as described above with reference to FIG. 10. The next step is to measure the background spectrum that is to say without a sample in position on the plate 67. In order to achieve this the user sets the mounting arm 100 to an arbitrary position on the guide pins 110 and 103 such that the sample contacting surface of the crystal is spaced from the plate 67 to thereby provide a crystal/air interface. The user then causes the stage to move to the origin, that is to say the top centre of the crystal and to fine focus on top of the crystal. The user can then select the resolution and pixel size. The system then operates automatically to raise the stage 20 by a predetermined distance based on the stored crystal height parameter in order to focus on the lower surface of the crystal (106). The system then carries out a measurement on the background spectrum for each detector in the array and these are stored. The way in which the background spectrum is obtained will be apparent to those skilled in the art.

The next step is to measure the crystal image and this involves the user moving the stage to the origin, i.e. the top centre of the crystal. The user fine focuses on the top of the crystal and then enters parameters such as the resolution, scans per pixel, pixel size and image size. The system raises the main stage 20 by a predetermined distance in order to focus on the lower surface of the crystal. The system measures the image of the crystal without a sample being present and this is stored.

The next step is to measure a sample and the first step is for a user to select an optional processing option which is subtraction of the background crystal image or baseline offset correction. The user then raises the arm 100 and pivots it about the pin 103 so that the crystal 106 is moved away from the optical axis of the microscope. The plate 67 on the anvil 60 is then removed and a sample located on that plate and the plate placed back in position on the anvil 60. The system then raises the stage by a predetermined distance in order to enable visual inspection of the sample using the visual facility of the microscope. The user mounts the sample in four sub-steps. These are:

(i) Mount the sample on the plate 67 and locate on the anvil 60.

(ii) Adjust the sample position using the sub-stage only, i.e. using the adjusting screws 70, 71 to adjust the position of the anvil (60). This is carried out whilst viewing the sample visually.

(iii) Swing the arm 100 back into position so that the crystal 106 is located on the optical axis of the microscope and lower the arm 100 thereby lowering the crystal 106 into contact with the sample on the plate 67.

(iv) Apply pressure to the underside of the top of the anvil 60 using the pressure applying mechanism 80 so that the sample is pressed into contact with the crystal.

With regard to (iv) ATR measurement requires that a sample is held in good contact with the lower face 112 of the crystal 106. Ideally the contact pressure should be reasonably uniform across the face of the crystal. For hard samples it is necessary for the sample to lie parallel to the crystal face; for most compliant samples control of the clamping force is required to prevent excessive sample deformation. With the sample on the plate 67 the arm 100 is lowered until the crystal just contacts the sample. The arm is locked using screws 111. The rack 91 is operated to apply a lifting force to the anvil 60 thus compressing the sample against the crystal face. This force is produced through the spring plunger 85 which is designed to restrict the maximum force to a value which avoids damage to the crystal 106. The force vector is important. Ideally it should be aligned with the centre of the crystal face so that samples tend to align to the face and contact pressure is uniform. This is achieved by use of the ball bearing 82 that is accurately constrained in its guide 83 and precisely aligned with the crystal axis. The ball acts against a thin part of the anvil so that the lifting force originates as close as possible to the crystal. The arrangement of the rack, pinion, spring plunger, lifting spring and ball is very compact in height and therefore significant in a microscope where there is limited space. The design of the spring plunger 85 ensures that the lifting spring 84 within the assembly is never compressed sufficiently to become coil bound and thus exert excessive force.

The screw 89 can be used to vary the pre-load on the spring. The maximum travel for the screw is set such that the spring never becomes coil-bound. With the screw set full clockwise the pre-load is approximately 50% of the maximum spring force. When the compression control knob is moved to the maximum pressure position the spring force increases close to the maximum rating of the spring. Backing off the screw 89 by one turn reduces the pre-load to zero. Thus with control at one end of its travel no force is imparted to the sample. As the user slides the control knob the compressive force gradually increases to 50% of the maximum possible spring force.

After sub-step (iv) the system then lowers the stage 20 by a predetermined distance in order to focus on the crystal top. The user fine focuses the registration mark on the top of the crystal if necessary. The user then enters the resolution, scans per pixel, wave number range, pixel size and image size and after this the system raises the stage 20 by a predetermined distance based on the stored crystal height parameter to focus on the sample. A measurement of the sample image is then taken in a manner which will be apparent to those skilled in the art. Where imaging is being carried out this involves making a first measurement, moving the microscope stage slightly to carry out a second measurement and repeating this for different positions on the microscope stage. Finally the system performs the selected post-processing and stores the image.

It should be understood that the motorised stage 20 is used for aligning the crystal 106 directly under the centre of the microscope field and for scanning the image around this centre. To align the sample the user should not use this motorised stage and this is the reason for the provision of the sub-stage 60. The software procedure can disable the moving mechanism of the motorised stage during sample viewing so that a user cannot inadvertently change the crystal registration.

Figure 11:
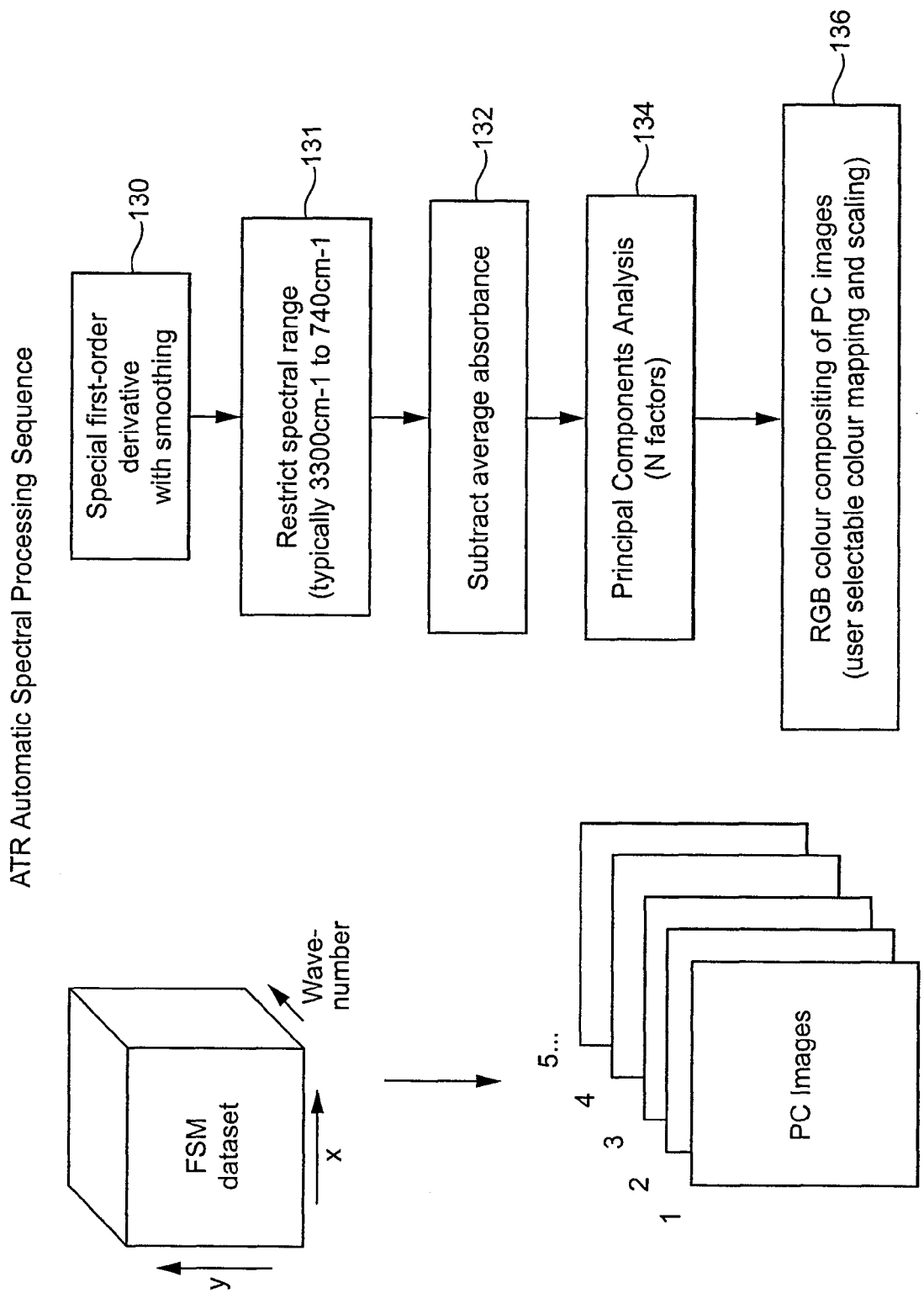

The arrangement is provided with a rapid automated spectral analysis procedure which is illustrated in FIG. 11 of the drawings. In many practical cases the sample presented for ATR analysis may have relatively weak overall absorption. ATR images showing total absorption obtained from such samples are often somewhat featureless or of very low contrast and illumination artifacts may obscure the details of the sample. Compensation for illumination effects is possible using conventional means such as ratios against background images or baseline correction which normalises spectra using regions known to have essentially zero absorption. It is possible also to process the data using advanced techniques in order to extract and display significant spectral features but this requires expertise in spectral signal processing and can be time consuming. In order to provide the user of the present system with a quick indication of the spectral information present in the image an automatic processing sequence has been devised. Its aim is to extract the most significant spectral features from the raw data in a manner which is independent of the sample and to permit the operator to display these either singly or in the form of colour composite images. The benefit to the user is the rapid confirmation that the image contains potentially useful information and a good preliminary analysis that provides guidance for further more advanced processing. For example the results can indicate which parts of the image are spectrally similar and which are distinct allowing the user to make a simple segmentation of the sample. The raw image may be acquired with either ratiometric correction against the background or baseline offset correction. The processing sequence begins with a step designed to minimise the effects of offsets and baseline curvature which is shown at 130 in FIG. 11. This involves differentiation in the spectral domain (first derivative with some degree of smoothing to reduce noise) and subtraction of any remaining average value. The spectral image is then restricted as shown at 131. At the short wave side a limit is set typically at about 3300 wave numbers since few samples show significant absorptions at shorter wavelengths. A small restriction is also made at the longwave end of the range to improve overall signal to noise. The average absorbance is then subtracted as shown at 132 and a principal components analysis is then applied as shown at 134 in order to extract the most significant spectral features. The components can then be presented to the user in an interface which allows them to be displayed as colour composite images as shown at 136.

The invention claimed is:

1. A device comprising:
    a support constructed and arranged to be coupled to a movable stage of a microscope;
    a mounting member on the support, the mounting member constructed and arranged to receive an attenuated total reflectance crystal at a first location;
    a sample supporting member disposed below the first location and on the support, the sample supporting member configured to be moveable relative to the first location; and
    a location adjustor configured to adjust a position of the sample supporting member on the support, the location adjustor comprising a pair of screws constructed and arranged to position the sample supporting member against a biasing spring,
    wherein a surface against which each screw acts is inclined at an angle to an axis of the crystal, whereby each screw is constructed and arranged to position the sample supporting member towards the support.

2. The device of claim 1, in which the sample supporting member comprises a substantially flat upper surface and side surfaces.

3. The device of claim 1, in which the screws are constructed and arranged to act along orthogonal directions and the biasing spring is constructed and arranged to act along a bisector of the orthogonal directions.

4. A microscope, comprising:
    an objective cassegrain;
    a condenser cassegrain;
    a moveable stage between the objective cassegrain and the condenser cassegrain; and
    an accessory device coupled to the moveable stage, the accessory device comprising:
        a support coupled to the movable stage;
        a mounting member on the support, the mounting member configured to receive an attenuated total reflectance crystal at a first location;
        a sample supporting member disposed below the first location and on the support, the sample supporting member configured to be moveable relative to the first location; and
        a location adjustor configured to adjust a position of the sample supporting member on the support, the location adjustor comprising a pair of screws constructed and arranged to position the sample supporting member against a biasing spring,
        wherein a surface against which each screw acts is inclined at an angle to an axis of the crystal, whereby each screw is constructed and arranged to position the sample supporting member towards the support.

5. The microscope of claim 4, further comprising an optic device optically coupled to at least one of the objective cassegrain and the condenser cassegrain.

6. The microscope of claim 5, further comprising a detector optically coupled to the optic device.

7. The microscope of claim 6, further comprising at least one minor optically coupled to at least one of the objective cassegrain and the condenser cassegrain.

8. The microscope of claim 7, in which the microscope is configured to operate in a reflectance mode.

9. The microscope of claim 4, in which the sample supporting member comprises a substantially flat upper surface and side surfaces.

10. The microscope of claim 4, in which the screws are constructed and arranged to act along orthogonal directions and the biasing spring is constructed and arranged to act along a bisector of the orthogonal directions.

11. A microscope, comprising:
    a moveable stage; and
    an accessory device coupled to the moveable stage, the accessory device comprising:
        a support coupled to the movable stage;
        a mounting member on the support and configured to receive an attenuated total reflectance crystal at a first location;
        a sample supporting member disposed below the first location and on the support, the sample supporting member configured to be moveable relative to the first location; and
        a location adjustor configured to adjust a position of the sample supporting member on the support, the location adjustor comprising a pair of screws constructed and arranged to position the sample supporting member against a biasing spring,
        wherein a surface against which each screw acts is inclined at an angle to an axis of the crystal, whereby each screw is constructed and arranged to position the sample supporting member towards the support.

* * * * *

UNITED STATES PATENT AND TRADEMARK OFFICE
CERTIFICATE OF CORRECTION

| | | |
|---|---|---|
| PATENT NO. | : 8,223,429 B2 | Page 1 of 1 |
| APPLICATION NO. | : 11/912478 | |
| DATED | : July 17, 2012 | |
| INVENTOR(S) | : Robert A. Hoult et al. | |

It is certified that error appears in the above-identified patent and that said Letters Patent is hereby corrected as shown below:

Column 14, Claim 7, Line 20, replace "one minor" with --one mirror--.

Signed and Sealed this
Eighteenth Day of December, 2012

David J. Kappos
*Director of the United States Patent and Trademark Office*